(12) United States Patent
Elten et al.

(10) Patent No.: US 6,245,362 B1
(45) Date of Patent: Jun. 12, 2001

(54) MEDICATION FOR TREATMENT OF VIRAL DISEASE BASED ON ACTIVE AGENTS OF PLANT HYPERICUM (ST. JOHN'S WORT) AND METHOD OF PRODUCTION OF THE MEDICATION

(75) Inventors: Holger Elten, Oldendorf; Annemarie Steinbeck-Klose, Bonn, both of (DE)

(73) Assignee: Dreluso Pharmazeutika Dr. Elten & Sohn GmbH, Oldendorf (DE)

( * ) Notice: Subject to any disclaimer, the term of this patent is extended or adjusted under 35 U.S.C. 154(b) by 0 days.

(21) Appl. No.: 09/091,472

(22) PCT Filed: Dec. 18, 1996

(86) PCT No.: PCT/DE96/02444

§ 371 Date: Jun. 17, 1998

§ 102(e) Date: Jun. 17, 1998

(87) PCT Pub. No.: WO97/22354

PCT Pub. Date: Jun. 26, 1997

(30) Foreign Application Priority Data

Dec. 18, 1995 (DE) ............................... 195 47 317

(51) Int. Cl.⁷ .................................... A61K 35/78
(52) U.S. Cl. ............................................ 424/730
(58) Field of Search ........................... 424/195.1

(56) References Cited

U.S. PATENT DOCUMENTS

| | | | |
|---|---|---|---|
| 4,898,891 | * 2/1990 | Lavie et al. | 514/732 |
| 5,047,435 | * 9/1991 | Lavie et al. | 514/732 |
| 5,049,589 | * 9/1991 | Lavie et al. | 514/732 |
| 5,120,412 | * 6/1992 | Mazur et al. | 204/157.87 |
| 5,288,485 | * 2/1994 | Kikuta et al. | 424/74 |
| 5,514,714 | * 5/1996 | Meruelo et al. | 514/561 |
| 5,820,867 | * 10/1998 | Bewicke | 424/195.1 |

FOREIGN PATENT DOCUMENTS

3935772 * 4/1991 (DE) .
79428 * 2/1983 (RO) .

OTHER PUBLICATIONS

Ozturk, Y. et al., Phytotherapy Research, vol. 6(1), p. 44–46, 1992.*

Meruelo, D. et al., Proc. Natl. Acad. Sci. USA, vol. 85(14), p. 5230–5234, Jul. 1988.*

* cited by examiner

Primary Examiner—Jean C. Witz
(74) Attorney, Agent, or Firm—Flanagan & Flanagan; John R. Flanagan; John K. Flanagan

(57) ABSTRACT

A medication for treatment of disease caused by virus, and particularly retrovirus, and a method of production of the medication are based on use of the active agents, polycyclic diones (hypericin, pseudohypericin and/or salts thereof), of the plant Hypericum (St. John's Wort) with other components occurring in the plant wherein the concentration of polycyclic diones is between 0.05% and 50% whereby a therapeutic antiretroviral effect is attained while undesirable side effects are largely avoided.

6 Claims, No Drawings

MEDICATION FOR TREATMENT OF VIRAL DISEASE BASED ON ACTIVE AGENTS OF PLANT HYPERICUM (ST. JOHN'S WORT) AND METHOD OF PRODUCTION OF THE MEDICATION

The invention relates to a medication for treatment of a disease caused by a virus, particularly a retrovirus, based on the active agents of the plant Hypericum (St. John's Wort) and to a method of production of the medication.

BACKGROUND OF THE INVENTION

The plant St. John's Wort as well as its applicability as a pharmaceutical were already known to people of antiquity. Most of the approximately 370 species of this plant worldwide comprise the red pigment hypericin, a naphthodianthrone derivative having a molecular weight of 504.43 and the empirical formula $C_{30}H_{16}O_8$. In addition to hypericin, a number of structural analogs was identified which have been described in the literature as pseudohypericin, protohypericin, protopseudohypericin, cyclopseudohypericin, isohypericin, Kielcortin etc., so-called polycyclic diones. Other components of the plant are, for example, the flavonoid quertecine as well as other bioflavonoids and flavonoid glycosides, vegetable acids such as chlorogenic and coffeic acid, hyperforin—a phloroglucine derivative—tanning agents, flower pigments as well as cyanidin chloride and xantophyll, anthraquinone, xanthone derivatives, distilled oils such as terpineol, resin-like substances, fats and waxes.

It has recently been found that polycyclic diones (hypericin, pseudohypericin and/or salts thereof) in highly pure form have antiviral efficacy. In particular, an inhibiting effect on retrovirus can be observed in vitro (cf. EP 0 332 697 B1); this applies also with respect to the human immunodeficiency virus (HIV) which in humans causes the acquired immune deficiency syndrome (AIDS). Hypericin or pseudohypericin were herein used in highly pure form. In order to obtain this form, the extract from the plant Hypericum was treated until nearly pure hypericin/pseudohypericin was obtained. Alternatively, highly pure hypericin was produced synthetically. The medications suggested in this connection comprised nearly pure hypericin/pseudohypericin (or pharmaceutically efficacious salts thereof) as the sole active agent, and, in addition, pharmacologically known solvents and carrier substances suitable in known manner for various forms of administration and dosages.

It has also been suggested to combine for the treatment of diseases caused by retrovirus the administration of hypericin/pseudohypericin with the administration of nucleoside analogs WO 89/09056. However, herein also nearly pure hypericin/pseudohypericin was used.

However, animal experiments have shown that when using highly pure hypericin/pseudohypericin, strong side effects in the form of hyperphotosensitization can occur. Due to this effect, the therapeutic application of preparations with highly pure hypericin/pseudohypericin must be ruled out. Therefore, this approach has not been pursued further and no Hypericum preparations for antiviral application have been introduced on the market.

In addition, in the field of medicine, Hypericum preparations have long been used based on extracts of the plant for various indications in the psychogenic area such as depressions in the absence of endogenous forms, sleep disorders and psychogenically caused other disorders such as bed wetting. An oily preparation from the plant (oleum hypericin) for external application in the treatment of wounds and pain is additionally known. The internal application of oleum hypericin has been recommended in the case of dyspeptic complaints.

The currently valid monograph by the Kommission E of the Bundesamt für Arzneimittel und Medizinprodukte (Federal Board for Pharmaceutical Drugs and Medical Products) lists as fields of application psychovegetative disorders, depressive states, anxiety and/or nervous agitation. All currently known Hypericum-containing pharmaceutical drugs concern this range of indications of psychogenic disorders and sleep disorders.

The known Hypericum-containing pharmaceutical drugs are based on the extract from the plant with a content of polycyclic diones (hypericin, pseudohypericin and/or salts thereof) of less than 1%. The listed active agents are thus not present in a pure state. The use of such preparations for the indications in viral illnesses is not known.

This range of indications had previously only been suggested for highly pure hypericin/pseudohypericin preparations but which, due to the above cited side effects, cannot be used therapeutically.

SUMMARY OF THE INVENTION

It is therefore the task of the invention to make therapeutically usable the antiviral, in particular antiretroviral, effect of polycyclic diones (hypericin, pseudohypericin and/or salts thereof) while largely avoiding the described side effects.

The invention rests on the surprising finding that the inhibition of retrovirus known for highly pure hypericin/pseudohypericin can also be attained with hypericin/pseudohypericin in lower concentrations provided sufficient dosages of hypericin/pseudohypericin are being administered. For this purpose, the active agents (hypericin, pseudohypericin and/or salts thereof) are mixed with other substances known to be components of the plant Hypericum or extracts are used which comprise the active agent (hypericin, pseudohypericin and/or salts thereof) in similarly low or slightly more concentrated form than in the preparations known for the treatment of psychogenic disorders and sleep disorders, thus in concentrations from between 0.05% and 50% of polycyclic diones, however these extracts do not {comprise the active agent} in highly pure form.

Surprisingly, herein the side effects known in connection with highly pure hypericin/pseudohypericin do not occur and specifically also in dosages which exceed by a multiple the dosages which had previously been used for Hypericum extract preparations for other indications (psychogenic disorders, sleep disorders). The extract obtained from the plant, with concentrations of polycyclic diones between 0.05% and 50% while retaining other substances comprised in the plant in concentration between 50% and 99.95% can consequently be used therapeutically for the treatment of viral diseases.

DETAILED DESCRIPTION OF PREFERRED EMBODIMENT

In a preferred embodiment the production of the dry extracts from the plant Hypericum perforatum Linne takes place according to the rules or the Deutsche Arzneibuch (German Pharmacopeia) (DAB) using ethanol 60% V/V. The dried and cut pharmaceutical is mixed with ethanol at a ratio of 1:4 (pharmaceutical to extraction agent) and allowed to stand for at least 14 days while stirring or shaking the mixture occasionally. Subsequently the supernatant is decanted and the residue pressed off.

Concentration of the polycyclic diones (hypericin and related substances) is achieved through the separation of high-molecular extract components by means of preparative gel chromatography (molecular sieves). Used are gels of the type Sephadex® G200.

From the liquid extract obtained according to the above process ethanol, water and volatile components are carefully removed in vacuo and specifically until a viscous brownish liquid forms. This is placed onto a preparative chromatography column and, in the course of the chromatography process, is separated into fractions of increasing molecular weight. The substances with the highest molecular weight appear last at the end of the column and are discarded.

By optimizing the elution conditions at the column in connection with continuous determination of the content, through the above described fractionation—by suitably selecting the desired fractions and discarding undesirable fractions—the content of the subsequent extracts of hypericin/pseudohypericin is determined with high accuracy to 1% g/g.

The desired fractions are collected and carefully dried in vacuo. The brownish powder obtained in the process with a content of hypericin/pseudohypericin of 1% g/g is used directly for the production of solid oral preparations.

A pharmaceutically acceptable carrier or a pharmaceutically acceptable dilution agent can be combined with the medication for facilitating its administration. The medication can be administered parenterally, in a solid form which can be administered rectally, in particular as a suppository, or in a solid form which can be administered orally, in particular a tablet, a coated tablet or a capsule, with or without a coating resistant to gastric juices.

In a further preferred embodiment, the solid form for oral administration is provided with a coating resistant to gastric juices. The resorption occurring thereby in the duodenum permits reducing the dose.

The medication can have a content of polycyclic diones (in particular hypericin) with a range of from 1 mg to 20 mg per parenteral dose, tablet, coated tablet, capsule or suppository, respectively.

Oral preparations such as for example capsules or tablets with dosages of the above described extract correspond to a quantity of 2 mg per dose, administered in daily doses of 6 mg and more over a relatively long period of time (at least 6 months) have the capability of bringing retrovirus in the serum below the minimum level of detection.

Consequently, the outbreak of diseases caused by retrovirus, such as for example AIDS, can be prevented.

What is claimed is:

1. A medication useful for treatment of a disease caused by a virus, comprising a therapeutically effective amount of an extract from the plant Hypericum (St. John's Wort) obtained by processes of ethanol extraction and preparative gel chromatography having a concentration of polycyclic diones of between 3% and 50% and more than one other naturally occurring component of the plant Hypericum (St. John's Wort) other than polycyclic diones of between 50% and 97%.

2. A method of producing a medication useful for treatment of a disease caused by a virus, comprising the steps of separating and fractionating by ethanol extraction and preparative gel chromatography an extract from the plant Hypericum (St. John's Wort) having a concentration of polycyclic diones of between 3% and 50% and of more than one other naturally occurring components of the plant Hypericum (St. John's Wort) other than polycyclic diones of between 50% and 97%.

3. The medication of claim 1, futher comprising a pharmaceutically acceptable carrier or a pharmaceutically acceptable dilution agent.

4. The method of claim 2, further comprising the step of mixing a pharmaceutically acceptable carrier or a pharmaceutically acceptable dilution agent with said extract.

5. The medication of claim 1, wherein the medication is in a form such that it can be administered parenterally, rectally, or orally. further comprising the step of providing the medication in a form such that it can be administered parenterally, rectally, or orally.

6. The method of claim 2, further comprising the step of providing the medication in a form such that it can be administered parenterally, rectally, or orally.

* * * * *